United States Patent [19]

Tanaka et al.

[11] Patent Number: 5,087,724
[45] Date of Patent: Feb. 11, 1992

[54] SUBSTITUTED BENZENES USEFUL AS INTERMEDIATES

[75] Inventors: Norio Tanaka; Takuya Kakuta; Eiichi Oya; Masatoshi Baba, all of Funabashi, Japan

[73] Assignee: Nissan Chemical Industries Ltd., Tokyo, Japan

[21] Appl. No.: 519,727

[22] Filed: May 7, 1990

Related U.S. Application Data

[62] Division of Ser. No. 360,468, Jun. 2, 1989, Pat. No. 4,942,246.

[30] Foreign Application Priority Data

Jun. 3, 1988 [JP] Japan ................... 63-137095
Apr. 18, 1989 [JP] Japan ..................... 1-98284

[51] Int. Cl.⁵ ............... C07C 323/09; C07C 323/20; C07C 323/62
[52] U.S. Cl. ..................... 558/425; 560/11; 560/18; 562/429; 562/432; 568/32; 568/39; 568/54; 568/56; 568/937
[58] Field of Search ........... 534/558; 558/412, 415, 558/416, 523, 425; 560/62, 65, 11, 18; 562/429, 432, 452; 568/32, 33, 35, 43, 39, 54, 56, 937

[56] References Cited

U.S. PATENT DOCUMENTS

| | | | |
|---|---|---|---|
| 1,974,689 | 9/1934 | Pfaff et al. | 560/65 X |
| 2,606,183 | 8/1952 | Head et al. | 534/558 X |
| 3,013,054 | 12/1961 | Richter | 560/65 |
| 3,211,611 | 10/1965 | Clark et al. | 560/18 |
| 3,689,546 | 9/1972 | Kirch | 558/425 |
| 3,855,285 | 12/1974 | Holland | 562/432 |
| 3,901,935 | 8/1975 | Dombnico | 558/425 X |
| 4,161,611 | 7/1979 | Kim | 534/558 X |
| 4,225,534 | 9/1980 | Yoshikawa | 558/425 |
| 4,470,930 | 9/1984 | Tang et al. | 558/425 |
| 4,582,948 | 4/1986 | Tang et al. | 558/425 X |
| 4,590,315 | 5/1986 | Maul et al. | 558/425 X |

FOREIGN PATENT DOCUMENTS

| | | | |
|---|---|---|---|
| 743581 | 9/1966 | Canada | 558/423 |
| 1933525 | 1/1971 | Fed. Rep. of Germany | 558/423 |
| 2550261 | 5/1977 | Fed. Rep. of Germany | 558/423 |

OTHER PUBLICATIONS

Nakada et al., Photochemical Delalogenations of Polyhalobenzenes Bulletin of the Chemical Society of Japan, 56(8) 2447-2451 (1983).

*Primary Examiner*—Mary C. Lee
*Assistant Examiner*—M. S. H. Gabilan
*Attorney, Agent, or Firm*—Oblon, Spivak, McClelland, Maier & Neustadt

[57] ABSTRACT

A process for producing a 4-benzoyl-5-hydroxyl-pyrazole of the formula III:

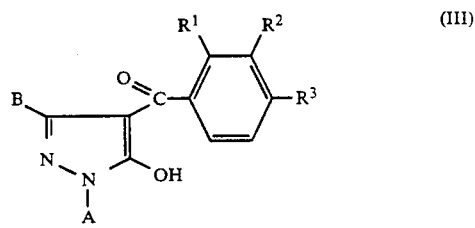

which comprises reacting carbon monoxide and a 5-hydroxypyrazole of the formula II:

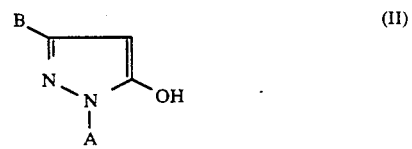

with a substituted benzene of the formula I:

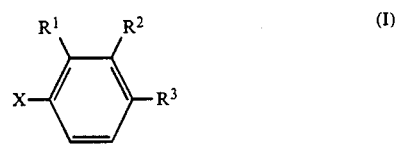

in the presence of a base and a catalyst of Group VIII of the Periodic Table.

34 Claims, No Drawings

SUBSTITUTED BENZENES USEFUL AS INTERMEDIATES

This is a division of application Ser. No. 07/360,468 filed on June 2nd 1989, now U.S. Pat. No. 4,942,246, granted July 17, 1990.

The present invention relates to a process for producing 4-benzoyl-5-hydroxypyrazoles useful as herbicides and substituted benzenes as their starting materials.

Certain compounds among 4-benzoyl-5-hydroxypyrazole derivatives are known to have herbicidal activities.

For example, pyrazolate (common name), pyrazoxyfen (common name) and benzofenap (common name) are practically used as herbicides for paddy fields.

Further, Japanese Patent Application No. 061349/1988 reports on 4-benzoyl-5-hydroxypyrazole derivatives which have selectivity for crop plants including not only rice but also corn, wheat, barley and sorghum as well as cotton, beet, soybean and rapeseed.

These herbicides are 4-benzoyl-5-hydroxypyrazoles themselves or their derivatives.

For the production of 4-benzoyl-5-hydroxypyrazoles, there have been known a process for their production from benzoic acids and 5-hydroxypyrazoles (Japanese Unexamined Patent Publication No. 138627/1976) and a process for their production from substituted benzenes, carbon tetrachloride and 5-hydroxypyrazoles (Japanese Unexamined Patent Publication No. 23668/1983).

However, the process for the production from benzoic acids and 5-hydroxypyrazoles are disadvantageous, since it requires expensive benzoic acids. On the other hand, in the process for the production from substituted benzenes, carbon tetrachloride and 5-hydroxypyrazoles, the substituents of the substituted benzenes must be inert to a Friedel-Craft catalyst. Further, the substituents are restricted to electron donative groups in order for the reaction to proceed smoothly.

Therefore, the above processes are not necessarily satisfactory, and an improved process for the production of 4-benzoyl-5-hydroxypyrazoles has been desired.

The present inventors have conducted researches with an aim to obtain 4-benzoyl-5-hydroxypyrazoles in an industrially advantageous manner and found a new process. The present invention has been accomplished on the basis of this discovery.

The present invention provides a process for producing a 4-benzoyl-5-hydroxypyrazole of the formula III:

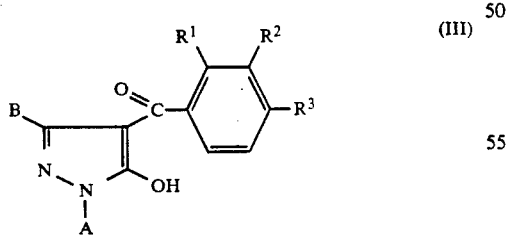

wherein A is an alkyl group having from 1 to 3 carbon atoms, an allyl group or a propargyl group, B is a hydrogen atom or a methyl group, $R^1$ is an alkyl group having from 1 to 4 carbon atoms, an alkoxy group having from 1 to 4 carbon atoms, a trifluoromethyl group, a nitro group, a cyano group or a halogen atom, $R^2$ is a hydrogen atom, an alkyl group having from 1 to 4 carbon atoms, an alkoxy group having from 1 to 4 carbon atoms, a hydroxy group, an alkoxyalkoxy group having from 3 to 6 carbon atoms, an alkoxyalkyl group having from 2 to 5 carbon atoms, an alkoxycarbonyl group having from 2 to 5 carbon atoms, a carboxyl group, a nitro group, a cyano group or a halogen atom, and $R^3$ is an alkylthio group having from 1 or 2 carbon atoms, an alkylsulfinyl group having 1 or 2 carbon atoms, an alkanesulfonyl group having 1 or 2 carbon atoms, a trifluoromethyl group, a nitro group, a cyano group or a halogen atom, which comprises reacting carbon monoxide and a 5-hydroxypyrazole of the formula II:

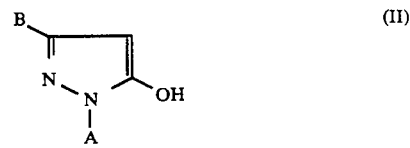

wherein A and B are as defined above, to a substituted benzene of the formula I:

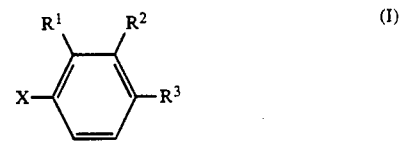

wherein X is a bromine atom, an iodine atom or a diazonium tetrafluoroboron salt group, $R^1$ is as defined above, provided that when X is a bromine atom, $R^1$ is a fluorine atom or a chlorine atom, and when X is an iodine atom, $R^1$ is a fluorine atom, a chlorine atom or a bromine atom, $R^2$ is as defined above, provided that when X is a bromine atom, $R^2$ is a fluorine atom or a chlorine atom, and when X is an iodine atom, $R^2$ is a fluorine atom, a chlorine atom or a bromine atom, and $R^3$ is as defined above, provided that when X is a bromine atom, $R^3$ is a fluorine atom or a chlorine atom, and when X is an iodine atom, $R^3$ is a fluorine atom, a chlorine atom or a bromine atom, in the presence of a base and a catalyst of Group VIII of the Periodic Table.

The present invention also provides a substituted benzene of the formula I' as a new compound, which is covered by the substituted benzene represented by the formula I:

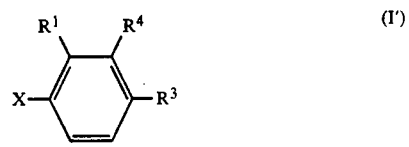

wherein X is a bromine atom, an iodine atom or a diazonium tetrafluoroboron salt group, $R^1$ is an alkyl group having from 1 to 4 carbon atoms, an alkoxy group having from 1 to 4 carbon atoms, a trifluoromethyl group, a nitro group, a cyano group or a halogen atom, provided that when X is a bromine atom, $R^1$ is a chlorine atom, and when X is an iodine atom, $R^1$ is a chlorine atom or a bromine atom, $R^3$ is an alkylthio group having 1 or 2 carbon atoms, an alkylsulfinyl group having 1 or 2 carbon atoms, an alkanesulfonyl group having 1 or 2 carbon atoms, a trifluoromethyl group, a nitro group, a cyano group or a halogen atom, provided that when X is a bromine atom, $R^3$ is a fluorine atom or a chlorine atom, and when X is an iodine atom, $R^3$ is a fluorine atom, a chlorine atom or a bromine atom, and $R^4$ is an alkyl group having from 1 to 4 carbon atoms, an alkoxy group having from 1 to 4 carbon atoms, a hydroxy group, an alkoxyalkoxy group having from 3 to 6 carbon atoms, an alkoxyalkyl group having from 2 to 5 carbon atoms, an alkoxycarbonyl group having from 2 to 5 carbon atoms, a carboxyl group, a nitro group, a cyano group or a halogen atom, provided that when X is a bromine atom, $R^4$ is a fluorine atom or a chlorine atom, and when X is an iodine atom, $R^4$ is a fluorine atom, a chlorine atom or a bromine atom.

Now, the present invention will be described in detail with reference to the preferred embodiments.

The substituents X, $R^1$, $R^2$, $R^3$ and $R^4$ of the substituted benzene of the formula I to be used in the process for the production of a 4-benzoyl-5-hydroxypyrazole of the formula III of the present invention and of the substituted benzene of the formula I' as the novel compound, include, for example, the following substituents:

X: Br, I, $N_2^+ \cdot BF_4^-$ $R^1$: Br (provided X=I or $N_2^+ \cdot BF_4^-$)
I (provided X=$N_2^+ \cdot BF_4^-$), $NO_2$, CN, F, Cl, Me, Et, n-Pr, i-Pr, OMe, OEt, OPr-h, OPr-i, $CF_3$ $R^2$: Br (provided X=I or $N_2^+ \cdot BF_4^-$)
I (provided X=$N_2^+ \cdot BF_4^-$), $NO_2$, CN, F, Cl, H, Me,
Et, n-Pr, i-Pr, OMe, OEt, OPr-n, OPr-i, OBu-n,
OBu-s, OBu-i, OBu-t, OH, $OCH_2CH_2OMe$, $OCH_2CH_2OEt$,
$OCH_2CH_2OPr$-n, $OCH_2CH_2OPr$-i, $CH_2OMe$, $CH_2OEt$,
$CH_2OPr$-n, $CH_2OPr$-i, $CH_2OBu$-n, $CH_2OBu$-s, $CH_2OBu$-i,
$CH_2OBu$-t, $CO_2Me$, $CO_2Et$, $CO_2Pr$-n, $CO_2Pr$-i, $CO_2Bu$-n, $CO_2Bu$-s, $CO_2Bu$-i, $CO_2Bu$-t, $CO_2H$, $R^3$: Br (provided X=I or $N_2^+ \cdot BF_4^-$)
I (provided X=$N_2^+ \cdot BF_4^-$), $NO_2$, CN, F, Cl, SMe, SEt, $SO_2Me$, $SO_2Et$, $CF_3$, $R^4$: Br (provided X=I or $N_2^+ \cdot BF_4^-$)
I (provided X=$N_2^+ \cdot BF_4^-$), $NO_2$, CN, F, Cl, Me, Et, n-Pr, i-Pr, OMe, OEt, OPr-n, OPr-i, OBu-n,
OBu-s, OBu-i, OBu-t, OH, $OCH_2CH_2OMe$, $OCH_2CH_2OEt$,
$OCH_2CH_2OPr$-n, $OCH_2CH_2OPr$-i, $CH_2OMe$, $CH_2OEt$,
$CH_2OPr$-n, $CH_2OPr$-i, $CH_2OBu$-n, $CH_2OBu$-s, $CH_2OBu$-i,
$CH_2OBu$-t, $CO_2Me$, $CO_2Et$, $CO_2Pr$-n, $CO_2Pr$-i, $CO_2Bu$-n,
$CO_2Bu$-s,
$CO_2Bu$-i, $CO_2Bu$-t, $CO_2H$ The substituents A and B of the 5-hydroxypyrazole of the formula II include, for example, the following substituents:

A: Me, Et, n-Pr, i-Pr, $CH_2CH=CH_2$, $CH_2C\equiv CH$
B: H, Me

The 5-hydroxypyrazole of the formula II is a tautomer of a 5-pyrazolone of the following formula II':

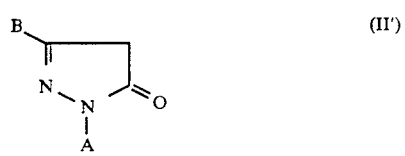

(II')

wherein A and B are as defined above, and it may be represented by either structural formula:

Now, the process for producing a substituted benzene of the formula I' as the compound of the present invention, will be described in detail.

Namely, the substituted benzene of the formula I' can be prepared, for example, by any one of the following reaction schemes:

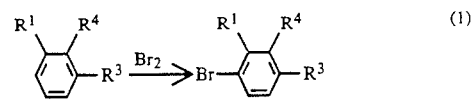

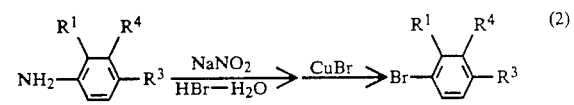

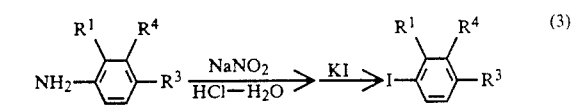

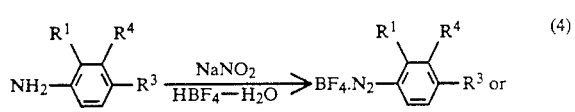

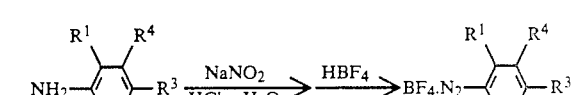

In the above formulas, $R^1$, $R^3$, $R^4$ and X are as defined above.

Reaction scheme (1) represents a reaction for preparing a substituted bromobenzene from a substituted benzene and bromine.

Bromine is used preferably in an amount of from 1.0 to 1.5 mols per mol of the substituted benzene. As a catalyst, an ion-reaction accelerator such as iron-iodine may be employed.

The solvent may be any solvent so long as it is inert to the reaction. For example, chloroform, carbon tetrachloride or acetic acid may be mentioned.

The reaction temperature is usually from $-20°$ C. to the refluxing temperature of the solvent, preferably from room temperature to $80°$ C.

The reaction is usually completed in 30 minutes to 24 hours.

Generally, the reaction of the reaction scheme (1) readily proceeds when the substituent $R^3$ is an electron donative group such as a methyl mercapto group.

The reaction scheme (2) represents a reaction for preparing a substituted bromobenzene wherein a substituted aniline is diazotized with sodium nitrite in hydrobromic acid to obtain a substituted benzene diazonium salt, which is then decomposed in hydrobromic acid containing copper bromide.

Sodium nitrite is used preferably in an amount of from 1.0 to 1.5 mols per mol of the substituted aniline. Hydrobromic acid may be at least 3.0 mols per mol of the substituted aniline.

Copper bromide is required to be from 0.01 to 2.0 mols per mol of the substituted aniline.

The diazotization reaction is conducted usually at a temperature of from −50° to 50° C., preferably from −20° C. to room temperature and is usually completed in 10 minutes to 5 hours.

The diazonium-decomposition reaction is accomplished usually in 10 minutes to 3 hours at a temperature of from room temperature to the refluxing temperature of hydrobromic acid.

Reaction scheme (3) represents a reaction for preparing a substituted iodobenzene, wherein a substituted aniline is diazotized with sodium nitrite in hydrochloric acid to obtain a substituted benzene diazonium salt, which is then decomposed in an aqueous potassium iodide solution.

Sodium nitrite is used preferably in an amount of from 1.0 to 1.5 mols per mol of the substituted aniline. Hydrochloric acid may be at least 2.0 mols per mol of the substituted aniline.

Potassium iodide is required to be from 1.0 to 1.5 mols per mol of the substituted aniline.

The diazotization reaction is conducted usually from −50° to 50° C., preferably from −20° C. to room temperature and is completed usually in 10 minutes to 5 hours.

The diazonium-decomposition reaction is completed usually in 10 minutes to 1 hour at a temperature of from room temperature to 100° C.

The reaction scheme (4) represents a reaction for preparing a substituted benzene diazonium tetrafluoroborate, wherein a substituted aniline is diazotized with sodium nitrite in tetrafluoroboric acid.

Sodium nitrite is used preferably in an amount of from 1.0 to 1.5 mols per mol of the substituted aniline, and tetrafluoroboric acid may be at least 2.0 mols per mol of the substituted aniline.

The reaction is conducted usually from −50° to 50° C., preferably from −20° C. to room temperature and is completed usually in 10 minutes to 1 hour.

It is also possible to prepare a substituted benzene diazonium tetrafluoroborate by diazotizing a substituted aniline in at least two equivalents of hydrochloric acid instead of tetrafluoroboric acid, to obtain a substituted benzene diazonium salt solution, and then at least an equivalent of tetrafluoroboric acid is added to the diazonium salt solution.

Reaction scheme (5) represents a reaction for preparing a substituted methanesulfonylbenzene by oxidizing a substituted methylmercaptobenzene. As the oxidizing agent, m-chloroperbenzoic acid, hydrogen peroxide-acetic acid and sodium hypochlorite may, for example, be mentioned.

The oxidizing agent is required in an amount of at least 2.0 equivalent to the substituted methylmercaptobenzene.

The solvent may be any solvent so long as it is inert to the reaction. The reaction may be conducted in the absence of a solvent.

The reaction is completed usually in 30 minutes to 24 hours at a temperature of from −20° to 120° C.

Now, the process for producing the 4-benzoyl-5-hydroxypyrazole of the formula III will be described in detail.

The substituted benzene of the formula I (including the substituted benzene of the formula I') is used usually from 0.1 to 10 mols, preferably from 0.3 to 5 mols, per mol of the 5-hydroxypyrazole.

Carbon monoxide may be pure gas. However, it may not necessarily be highly pure and may be a gas mixture diluted with an inert gas such as nitrogen gas or carbon dioxide gas.

The amount of carbon monoxide may be at least one mol per mol of the substituted benzene of the formula I.

The pressure of carbon monoxide is usually from atmospheric pressure to 150 kg/cm$^2$, preferably atmospheric pressure to 100 kg/cm$^2$. The catalyst of Group VIII of the Periodic Table to be used in the process of the present invention, may be a simple substance of metal such as cobalt, palladium, platinum, rhodium, ruthenium, iridium or osmium. Such a metal may be used alone or may be used as supported on a carrier such as graphite, silica gel, alumina, silica-alumina or molecular sieve.

Further, their metal salts such as acetates, carbonates, nitrates, chlorides and bromides may be employed. For example, cobalt acetate, palladium acetate, cobalt carbonate, palladium chloride, cobalt chloride and ruthenium bromide may be mentioned.

Further, their metal complexes may be mentioned. As the ligand of such a metal complex, there may be mentioned, for example, triphenylphosphine, tri-o-tolylphosphine, tri-m-tolylphosphine, tri-p-tolylphosphine, 1,2-bis(diphenylphosphino)butane, tri-n-butylphosphine, triethylphosphine, benzonitrile or carbon monoxide. Specific examples of the metal complexes include, for example, $PdCl_2[P(o-Me-Ph)_3]_2$, $PdCl_2[P(m-Me-Ph)_3]_2$,
$PdCl_2[P(p-Me-Ph)_3]_2$, $PdCl_2(PMe_3)_2$, $HCo(CO)_4$,
$Co_2(CO)_8$, $PdCl_2(PPh_3)_2$, $PdBr_2(PPh_3)_2$, $Pd(PPh_3)_4$,
$PdCl_2[P(Ph)_2CH_2CH_2P(Ph)_2]$, $PdCl_2(PhCN)_2$,
$Pd(CO)(PPh_3)_3$, $RhCl(PPh_3)_3$, $RhCl(CO)(PPh_3)_2$,
$Pt(CO)_2(PPh_3)_2$, $H_4Ru(CO)_{12}$ and $Ru_3(CO)_{12}$.

In some cases, the ligand may be added to the reaction system in an amount in excess of the amount required for forming a metal complex.

The catalyst of Group VIII of the Periodic Table is used usually in an amount of from 0.0001 to 150 g atom, preferably from 0.001 to 100 g atom as metal per mol of the substituted benzene of the formula I.

The base to be used together with the catalyst may be an amine such as triethylamine, tri-n-butylamine, pyridine, dimethylaniline or tetramethylurea, an organic carboxylate such as sodium acetate or potassium propionate, or an inorganic base such as sodium carbonate, potassium carbonate, sodium hydrogencarbonate, calcium oxide, sodium hydroxide, potassium hydroxide or calcium hydroxide. The base is used usually in an amount of from 0.1 to 100 mols, preferably from 1.0 to 30 mols, per mol of the substituted benzene of the formula I.

The reaction may be conducted in an inert solvent or in the absence of a solvent.

The solvent may be an ether such as diethyl ether, diethylene glycol dimethyl ether, tetrahydrofuran or dioxane, an aromatic hydrocarbon such as benzene, toluene, xylene, nitrobenzene or chlorobenzene, a nitrile such as acetonitrile or benzonitrile, N,N-dimethylacetamide, N,N-dimethylformamide, N-methylpyrrolidone, dimethylsulfoxide or hexamethylphosphoramide.

The reaction temperature is usually from room temperature to 250° C., preferably from 80° to 200° C.

The reaction time is usually from 0.5 to 300 hours, preferably from 1 to 70 hours.

Now, the preparation of the substituted benzene of the formula I is described in detail with reference to Examples. However, it should be understood that the present invention is by no means restricted by these specific Examples.

EXAMPLE 1-1

Preparation of 2,4-dichloro-3-methylbromobenzene

To a solution of 48.8 g (0.3 mol) of 2,6-dichlorotoluene in 60 ml of carbon tetrachloride, 0.7 g of iron powder and 0.1 g of iodine were added. Then, 52.8 g (0.33 mol) of bromine was dropwise added thereto at room temperature while maintaining the reaction temperature at a level of from 22° to 25° C. After completion of the dropwise addition, the reaction was continued at the same temperature until generation of hydrogen bromide ceased.

After the reaction, the reaction solution was added to 300 ml of ice water and extracted with 300 ml of 1,2-dichloroethane.

The organic layer was separated and washed sequentially with water, a saturated sodium hydrogen sulfite aqueous solution, water and a saturated sodium chloride aqueous solution. Then, the solvent was distilled off under reduced pressure to obtain 71.9 g (yield: 99.5%) of desired 2,4-dichloro-3-methylbromobenzene.

Melting point: 32°–33° C.

EXAMPLE 1-2

Preparation of 4-bromo-3-chloro-2-methoxycarbonylohenyl methyl sulfone (1) 3-Chloro-2-methylphenyl methyl sulfide To a solution of 161 g (1 mol) of 2,6-dichlorotoluene in 700 ml of hexamethylphosphoramide, 105 g (1.5 mol) of sodium methanethiolate was added, and the mixture was reacted at 100° C. for 30 minutes.

After the reaction, the reaction solution was returned to room temperature, and 35.5 g (0.25 mol) of methyl iodide was added thereto and stirred. Further, 1 l of water was added thereto, and the mixture was extracted three times with 500 ml of diethyl ether.

The ether layer was washed twice with water and dried over anhydrous sodium sulfate. Then, the solvent was distilled off under reduced pressure.

Then, distillation under reduced pressure was conducted to obtain 132.8 g (yield: 77%) of the desired product.

Boiling point: 107°–110° C./10 mmHg.

(2) 4-Bromo-3-chloro-2-methylphenyl methyl sulfide 34.5 g (0.2 mol) of 3-chloro-2 methylphenyl methyl sulfide was dissolved in 50 ml of carbon tetrachloride, and 0.5 g of iron powder and 0.1 g of iodine were added thereto. Then, 35.2 g (0.22 mol) of bromine was dropwise added at a reaction temperature of 30° C. Thereafter, the reaction was continued at the same temperature until generation of hydrogen bromide ceased.

Then, the same treatment as in Example 1-1 was conduced, followed by distillation under reduced pressure to obtain 47.8 g (yield: 95%) of the desired product.

Boiling point: 104.5°–106° C./0.04 mmHg.

(3) 4-Bromo-3-chloro-2-methylphenyl methyl sulfone

To 23.6 g (0.09 mol) of 4-bromo-3-chloro-2-methylphenyl methyl sulfide, 50 ml of a 35% hydrogen peroxide aqueous solution and 50 ml of acetic acid were added, and the mixture was reacted at 80° C. for 4 hours.

After the reaction, the reaction solution was added to 300 ml ice water. Precipitated crystals were collected by filtration, then washed with water and dried to obtain 25.5 g (yield: 100%) of the desired product.

Melting point: 144°–145° C.

(4) 3-Bromo-2-chloro-6-methanesulfonylbenzoic acid 10.0 g (35 mmol) of 4-bromo-3-chloro-2-methylphenyl methyl sulfone was added to 150 ml of acetic acid to obtain a uniform solution at 80° C. Thereto, 31.6 g (0.2 mol) of potassium permanganate was portionwise added to maintain the reaction temperature at a level of not higher than 85° C., and the reaction was conducted.

From the reaction solution, acetic acid was distilled off under reduced pressure. Then, 200 ml of a 5% potassium hydroxide aqeuous solution was added, and insoluble substances were separated by filtration. To the aqueous solution thus obtained, concentrated hydrochloric acid was added to adjust the pH to a level of not higher than 1, and water was distilled off under reduced pressure. To the residue, ethyl acetate was added, and insoluble salts were separated by filtration. Then, the solvent was distilled off under reduced pressure to obtain 3.7 g of the desired product.

Characteristic: glassy solid
$^1$H NMR ($\delta$, ppm, CDCl$_3$-DMSO-d$_6$):
3.22(3H, s), 7.9(2H, A-Bq), 8.73(1H,s)

(5) Methyl 3-bromo-2-chloro-6-methanesulfonylbenzoate

To 3.7 g of 3-bromo-2-chloro-6-methanesulfonylbenzoic acid, 10 ml of thionyl chloride and 0.1 g of N,N-dimethylformamide were added, and the mixture was reacted for 2 hours at the refluxing temperature. Then, toluene was added thereto, and excess thionylchloride was distilled off.

The reaction solution was returned to room temperature, and 30 ml of methanol was gradually added thereto. The mixture was reacted for 3 hours under stirring, and then methanol was distilled off.

The residue was dissolved in ethyl acetate and washed sequentially with water and a saturated sodium chloride aqueous solution. Then, the solvent was distilled off to obtain 3.72 g of the desired product.

Melting point: 67°–69° C.

Example 1-3

Preparation of 4-bromo-3-chloro-2-methoxymethylphenyl methyl sulfone (1) 4-Bromo-2-bromomethyl-3-chlorophenyl methyl sulfone A solution comprising 50.0 g of 4-bromo-3-chloro-2-methyl phenyl methylsulfone and 500 g of carbon tetrachloride, was refluxed under heating, and 37.0 g of bromine was dropwise added while irradiating white light.

After completion of the dropwise addition, refluxing was continued under heating for further 3 hours while irradiating white light. The reaction mixture was left to cool, and then chloroform was added thereto. The organic layer was separated and washed sequentially with a aqueous sodium hydrogensulfite solution and water. The organic layer was dried over sodium sulfate, and the solvent was distilled off under reduced pressure to obtain 63.5 g of the desired product.

(2) 4-Bromo-3-chloro-2-methoxymethylchenyl methyl sulfone

To a suspension comprising 8.5 g of 4-bromo-2-bromomethyl-3-chlorophenyl methyl sulfone and 100 ml of methanol, 1.5 g of sodium methoxide (95%) was added under cooling with ice, and then the mixture was stirred at room temperature overnight.

The reaction solution was concentrated, and water was added thereto. The mixture was extracted with chloroform. The extract was washed sequentially with dilute hydrochloric acid and water and dried over sodium sulfate. Then, the solvent was distilled off under reduced pressure to obtain 7.2 g of the desired product.

EXAMPLE 1-4

Preparation of 3′-iodo-6′-methanesulfonyl-2′-methylbenzyl methyl ether

(1) 2-Methyl-3-nitrobenzyl alcohol 39.0 g (0.2 mol) of methyl 2-methyl-3-nitrobenzoate was dissolved in 600 ml of tert-butanol. Then, 19.0 g of sodium borohydride was added thereto, and 150 ml of methanol was further dropwise added over a period of one hour at the refluxing temperature. Further, refluxing was continued for one hour to complete the reaction.

The reaction mixture was left to cool, and water was added thereto. The solvent was distilled off under reduced pressure.

To the residue, water and chloroform were added. The organic layer was separated and dried over anhydrous sodium sulfate. Further, the solvent was distilled off to obtain 30.7 g of 2-methyl-3-nitrobenzyl alcohol.

(2) 2-Methyl-3-nitrobenzyl methyl ether 30.1 g (0.18 mol) of 2-methyl-3-nitrobenzyl alcohol obtained above, was dissolved in 200 ml of benzene. Then, 0.2 g of tetra-n-butylammonium bromide and a 50% aqueous solution containing 20.1 g of sodium hydroxide were sequentially added thereto. Then, 27.2 g of dimethyl sulfate was dropwise added thereto at room temperature, and the mixture was further stirred for 3 hours for reaction.

To the reaction solution, water was added. The organic layer were separated and washed sequentially with water, a 2% hydrochloric acid aqueous solution, water and a saturated sodium chloride aqueous solution. Then, the solvent was distilled off to obtain 30.9 g of 2-methyl-3-nitrobenzyl methyl ether. Oily substance.

(3) 3-Methoxymethyl-2-methylaniline

To 30.7 g (0.17 mol) of the above 2-methyl-3-nitrobenzyl methyl ether, 200 ml of methanol was added and dissolved. Then, 92 ml of concentrated hydrochloric acid was gradually added. Then, 30.4 g of iron powder was gradually added so that the reaction temperature became not higher than 60° C., and the reaction was continued for further one hour.

To the reaction solution, 300 ml of water was added, and sodium hydroxide was added until the solution became at least pH 8.

To the slurry thereby obtained, chloroform was added and thoroughly stirred. Then, solid was separated by filtration. From the filtrate, the organic layer was separated. This organic layer was washed sequentially with water and a saturated sodium chloride aqueous solution, and then dried over anhydrous sodium sulfate. Further, the solvent was distilled off under reduced pressure to obtain 23.1 g of 3-methoxymethyl-2-methylaniline. Oily substance.

(4) 3-Methoxymethyl-2-methyl-4-thiocyanoaniline 22.6 g (0.15 mol) of 3-methoxymethyl-2-methylaniline was dissolved in 300 ml of methanol, and then 36.5 g of sodium thiocyanate was added to obtain a uniform solution. This solution was cooled to 0° C., and a solution of 25.2 g of bromine in 100 ml of sodium bromide-saturated methanol, was dropwise added thereto so that the reaction temperature did not exceed 5° C. After the dropwise addition, stirring was continued for one hour at a temperature of not higher than 5° C. and further at room temperature for one hour to complete the reaction.

The reaction solution was added to 1 l of water and neutralized with a 5% sodium carbonate aqueous solution. Chloroform was added thereto, and the oil component was extracted. The chloroform layer was washed with water and a saturated sodium chloride aqueous solution and dried over anhydrous sodium sulfate. The solvent was distilled off under reduced pressure to obtain 29.6 g of the desired product.

(5) 3-Methoxymethyl-2-methyl-4-methylthioaniline 29.1 g (0.14 mol) of 3-methoxymethyl-2-methyl-4-thiocyanoaniline was dissolved in 200 ml of ethanol and mixed with an aqueous solution comprising 33.6 g of sodium sulfide nonahydrate and 100 ml of water at room temperature.

Then, 21.9 g of methyl iodide was dropwise added thereto, and the mixture was reacted at room temperature for 3 hours.

After completion of the reaction, the solvent was distilled off under reduced pressure, and the residue was concentrated. Water and chloroform were added thereto, and the organic layer was separated. The organic layer thus obtained was washed sequentially with water and a saturated sodium chloride aqueous solution, and then dried over anhydrous sodium sulfate. The solvent was distilled off under reduced pressure to obtain 25.6 g of the desired product. Oily substance.

(6) 3′-Iodo-2′-methyl-6′-methylthiobenzyl methyl ether

To 25.6 g (0.13 mol) of 3-methoxymethyl-2-methyl-4-methylthioaniline, 100 ml of water and 33 ml of concentrated hydrochloric acid were added to obtain an aniline hydrochloride. Then, this solution was cooled to 0° C. and a solution cf 9.3 g of sodium nitrite in 30 ml of water, was dropwise added so that the reaction temperature did not exceed 5° C. After completion of the dropwise addition, the stirring was continued for further 30 minutes to complete the diazotization.

A solution of 33 g of potassium iodide in 100 ml of water, was heated to 70° C., and the aqueous solution of the diazonium salt obtained above was gradually added and decomposed. The reaction solution was stirred at 70° C. for further one hour and then left to cool. The oil component was extracted with benzene. The benzene layer was washed sequentially with water, a saturated sodium hydrogensulfite aqueous solution, water and a saturated sodium chloride aqueous solution. Then, the solvent was distilled off under reduced pressure, and the residue was purified by column chromatography (eluent: benzene) to obtain 30.0 g of the desired product.

Melting point: 56.0°–59.0° C.

(7) 3'-Iodo-6-'-methanesulfonyl-2'-methylbenzyl methyl ether

To 3.08 g of 3'-iodo-2'-methyl-6'-methylthiobenzyl methyl ether, 10 ml of acetic acid and 10 ml of a 35% hydrogen peroxide aqueous solution were added, and the mixture was reacted at 60° C. for 5 hours.

The reaction mixture was left to cool, and then 100 ml of water was added to the reaction solution. The mixture was extracted twice with ethyl acetate. The ethyl acetate layer was washed sequentially with a saturated sodium hydrogencarbonate aqueous solution, water and a saturated sodium chloride aqueous solution, and then dried over anhydrous sodium sulfate. The solvent was then distilled off under reduced pressure. The residue thereby obtained was purified by silica gel column chromatography (eluent: chloroform/ethyl acetate=19/1) to obtain 3.05 g of the desired product. Melting point: 77°-78° C.

EXAMPLE 1-5

Preparation of methyl 3-iodo-6-methanesulfonyl-2-methyl benzoate (1) Methyl 3-amino-2-methyl benzoate 40 g of methyl 2-methyl-3-nitrobenzoate was dissolved in 120 ml of methanol, and 157 g of concentrated hydrochloric acid was added thereto. Then, while maintaining the mixture at the temperature of not higher than 60° C., 36.8 g of iron powder was gradually added in small portions. The mixture was stirred at room temperature for 4 hours and then put into 1 l of ice water. The mixture was neutralized with sodium carbonate and extracted with chloroform, (insolubles were removed by filtration in this process). The extract was washed with a saturated sodium chloride aqueous solution and dried over anhydrous sodium sulfate. The solvent was distilled off to obtain 27.8 g of the desired product. Oily substance.

(2) Methyl 3-amino-2-methyl-6-thiocyanobenzoate

A solution comprising 27.7 g of methyl 3-amino-2-methyl benzoate, 41.5 g of sodium thiocyanate and 250 ml of methanol, was maintained at a temperature of not higher than 0° C., and a solution comprising 100 ml of a sodium bromide-saturated methanol and 28.1 g of bromine was gradually dropwise added thereto. The mixture was stirred at room temperature for 3 hours and then put into 1 l of ice water. The mixture was neutralized with sodium carbonate and extracted with chloroform. The extract was washed with a saturated sodium chloride aqueous solution and dried over anhydrous sodium sulfate. The solvent was distilled off to obtain 34.0 g of the desired product. Oily substance.

(3) Methyl 3-amino-2-methyl-6-methylthiobenzoate

To a solution comprising 39.5 g of sodium sulfide nonahydrate and 110 ml of water, a solution comprising 32.9 g of methyl 3-amino-2-methyl-6-thiocyanobenzoate and 300 ml of ethanol, was dropwise added. The mixture was stirred at room temperature for 1.5 hours, and then 24 g of methyl iodide was dropwise added thereto under cooling with ice. The mixture was stirred at room temperature for 2 hours and then concentrated under reduced pressure. A saturated sodium chloride aqueous solution was added thereto, and the mixture was extracted with chloroform. The chloroform layer was dried over anhydrous sodium sulfate, and then the solvent was distilled off to obtain 30.1 g of the desired product. Oily substance.

(4) Methyl 3-iodo-2-methyl-6-methylthiobenzoate 28 g of methyl 3-amino-2-methyl-6-methylthiobenzoate was stirred in 150 ml of concentrated hydrochloric acid at room temperature for 2 hours to obtain its hydrochloride. Then, while maintaining the temperature at a level of not higher than 0° C., a solution comprising 11.9 g of sodium nitrite and 20 ml of water, was dropwise added to obtain a diazonium salt solution. A solution comprising 28.4 g of potassium iodide and 90 ml of water, was maintained at 80° C., and the diazonium salt solution was dropwise added thereto. After completion of the dropwise addition, the mixture was stirred at 80° C. for 15 minutes and then left to cool. Water was added thereto, and the mixture was extracted with chloroform. The extract was washed with an aqueous sodium hydrogensulfite solution and water and then dried over anhydrous sodium sulfate. The solvent was distilled off to obtain 40 g of a crude of the desired product. The crude was purified by silica gel chromatography (developed with benzene) to obtain 36.0 g of the desired product. Oily substance.

(5) 3-Iodo-4-methanesulfonyl-2-methanesulfonyl-2-methylbenzoic acid

The desired product was prepared in accordance with Example 1-4-(7). Melting point: 66°-67° C.

EXAMPLE 1-6

Preparation of methyl 3-bromo-2-methyl-6-methylthiobenzoate 16.1 g of methyl 3-amino-2-methyl-6-methylthiobenzoate was stirred in 150 ml of hydrobromic acid (48%) to obtain its hydrobromide. While maintaining the temperature at a level of not higher than 0° C., a solution comprising 7.2 g of sodium nitrite and 20 ml of water, was dropwise added to obtain a diazonium salt solution.

A solution comprising 6.0 g of cuprous bromide and 7.7 g of hydrobromic acid (48%) was refluxed under heating, and the diazonium salt solution was dropwise added thereto. After completion of the dropwise addition, the mixture was refluxed under heating for further one hour and then left to cool. Ice water was added thereto, and the mixture was extracted with chloroform. The extract was washed with an aqueous sodium-hydrogen sulfite solution and water, and then dried over anhydrous sodium sulfate. The solvent was distilled off to obtain 19.2 g of a crude of the desired product. The crude was purified by silica gel column chromatography (eluent: benzene) to obtain 17.1 g of the purified desired product. Oily substance.

EXAMPLE 1-7

Preparation of methyl 2-chloro-3-iodo-6-methylthiobenzoate

The desired product was prepared in the same manner as in Example 1-5. Oily substance.

EXAMPLE 1-8

Preparation of 4-bromo-3-chloro-2-isoprocoxymethylphenyl methyl sulfone

To a suspension comprising 20.0 g of 4-bromo-2-bromomethyl-3-chlorophenyl methyl sulfone and 200 ml of isopropanol, 100 ml of an isopropanol solution of sodium isopropoxide (prepared from 1.4 g of metal sodium) was added at room temperature, and the mixture was stirred overnight. The post treatment was conducted in the same manner as in Example 1-3-(2) to obtain 18.4 g of the desired product.

Melting point: 87°-91° C.

In Table 1, the physical properties of the substituted benzenes of the formula I will be given.

TABLE 1

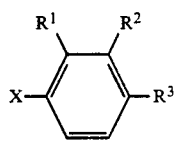

| Comp. No. | X | R¹ | R² | R³ | m.p. (°C.) |
|---|---|---|---|---|---|
| 1 | I | CN | H | SMe | 189~194 |
| 2 | I | OMe | H | SMe | Oily |
| 3 | I | NO₂ | H | CF₃ | Oily |
| 4 | Br | Cl | CO₂Me | SO₂Me | 67~69 |
| 5 | Br | Cl | CO₂H | SO₂Me | Oily |
| 6 | I | Cl | CO₂Me | SMe | Oily |
| 7 | I | Cl | CO₂H | SMe | 155~159 |
| 8 | I | Cl | CO₂Pr-i | SMe | Oily |
| 9 | Br | Me | CO₂Me | SMe | Oily |
| 10 | Br | Me | CO₂H | SMe | 98~103 |
| 11 | Br | Me | CO₂Pr-i | SMe | Oily |
| 12 | I | Me | CO₂Me | SMe | Oily |
| 13 | I | Me | CO₂Me | SO₂Me | 66~67 |
| 14 | I | Me | CO₂Et | SMe | Oily |
| 15 | I | Me | CO₂Pr-i | SMe | Oily |
| 16 | I | Me | CO₂CH₂CH₂OMe | SMe | Oily |
| 17 | I | Me | CO₂CH₂CH₂Cl | SMe | Oily |
| 18 | I | OMe | CO₂Me | SMe | 78~80 |
| 19 | Br | Cl | CH₂OMe | SO₂Me | 72~74 |
| 20 | I | Cl | CH₂OMe | SMe | 53~56 |
| 21 | I | Me | CH₂OMe | SO₂Me | 77~78 |
| 22 | I | Me | CH₂OMe | SMe | 56~59 |
| 23 | I | Me | CH₂OEt | SMe | Oily |
| 24 | I | Me | CH₂OPr-i | SMe | Oily |
| 25 | I | OMe | CH₂OMe | SMe | Oily |
| 26 | I | Me | CHMeOMe | SMe | Oily |
| 27 | I | Me | CHMeOEt | SMe | Oily |
| 28 | I | Me | CHEtOMe | SMe | Oily |
| 29 | I | Me | OMe | SMe | Oily |
| 30 | I | Cl | Cl | SMe | Oily |
| 31 | I | Me | NO₂ | SMe | bp. 135~145° C./0.1 mmHg |
| 32 | Br | Cl | Me | SO₂Me | 144~145 |
| 33 | Br | Cl | Me | SMe | bp. 102~105° C./0.03 mmHg |
| 34 | I | Cl | CN | Cl | 139~144 |
| 35 | Br | Cl | Me | Cl | Oily |
| 36 | Br | Cl | CH₂OPr-i | SO₂Me | 87~91 |

Now, the process for producing the 4-benzoyl-5-hydroxypyrazole of the formula III derived from the substituted benzene of the formula I, will be described with reference to Examples. However, it should be understood that the present invention is by no means restricted by such specific Examples.

EXAMPLE 2-1

Preparation of 1-ethyl-5-hydroxy-4-(3-methoxymethyl-2-methyl-4-methylthiobenzoyl)pyrazole 2.0 g of 3-methoxymethyl-2-methyl-4-methylthioiodobenzene, 1.46 g of 1-ethyl-5-hydroxypyrazole, 0.65 g of triethylamine, 4.04 g of anhydrous potassium carbonate, 0.28 g of dichloro(bistriphenylphosphine)palladium and 50 ml of 1,4-dioxane were charged into a 100 ml of Hastelloy autoclave equipped with a rotary stirrer, and the interior of autoclave was substituted with carbon monoxide, then, carbon monoxide was injected under a pressure of 10 kg/cm². Then, the temperature was gradually raised under stirring, and the reaction was continued at 140° C. for 8 hours. The reaction mixture was left to cool, and then unreacted carbon monoxide was purged. The reaction solution was taken out, and the solvent was distilled off under reduced pressure. Then, water and chloroform were added, and the mixture was subjected to liquid separation. The aqueous layer was washed with chloroform, and insoluble substances were separated by filtration. Concentrated hydrochloric acid was added to bring the pH to a level of not higher than 1. Then, chloroform was added thereto, and the mixture was extracted twice. The organic layer was washed with a saturated sodium chloride aqueous solution and dried over anhydrous sodium sulfate. Then, the solvent was distilled off under reduced pressure to obtain 1.75 g of a crude of the desired product (yield: 84%). Oily substance.

EXAMPLE 2-2

Preparation of 4-(2-chloro-4-methanesulfonyl-3-methylbenzoyl)-1-ethyl-5-hydroxypyrazole 1.42 g of 2-chloro-4-methanesulfonyl-3-methyl-bromobenzene, 2.24 g of 1-ethyl-5-hydroxypyrazole, 10 ml of triethylamlne, 0.175 g of dichloro(bistriphenyl-phosphine)palladium and 50 ml of dry 1,4-dioxane were charged into a 100 ml stainless steel autoclave equipped with a rotary stirrer, and the interior of the autoclave was substituted by carbon monoxide. Then, carbon monoxide was injected under a pressure of 20 kg/cm². Then, the reaction temperature was raised to 150° C. under stirring, and the reaction was continued for 9 hours. The reaction mixture was left to cool and treated in the same manner as in Example 2-1 to obtain 0.60 g of the desired product (yield: 43%).

Melting point: 225°-227° C.

In the following Tables 2 to 5, Examples of the present invention under various conditions will be given.

Further, the physical properties of the 4-benzoyl-5-hydroxypyrazoles of the formula III will be given in Table 6.

TABLE 2

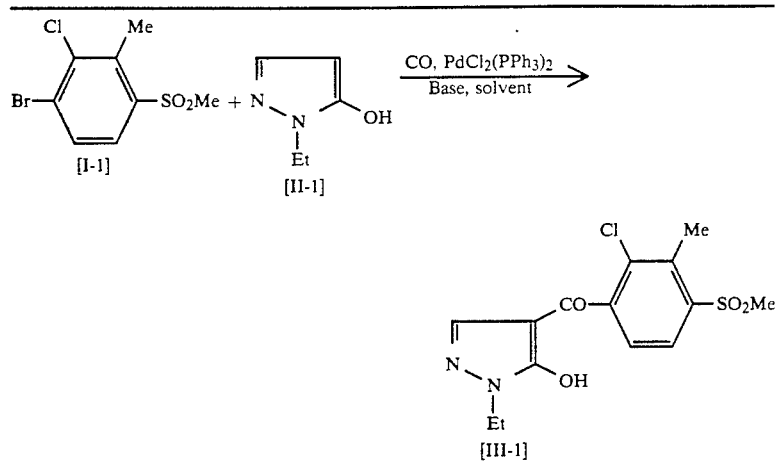

| Ex. No. | Solvent (50 ml) | Base (mmol) | CO pressure (kg/cm$^2$) | Temp. (°C.) | Time (hr) | Conversion (%*) | Isolated yield (%*) |
|---|---|---|---|---|---|---|---|
| 2-3 | dioxane | Et$_3$N(72) | 50 | 150 | 4.5 | 100 | 60 |
| 2-4 | dioxane | Et$_3$N(72) | 50 | 120 | 20 | 100 | 55 |
| 2-5 | dioxane | Et$_3$N(72) | 50 | 100 | 18 | 61 | 29 |
| 2-6 | dioxane | Et$_3$N(20) K$_2$CO$_3$(10) | 20 | 150 | 7 | 100 | 62 |
| 2-7 | dioxane | Et$_3$N(20) K$_2$CO$_3$(10) | 50 | 150 | 7.5 | 100 | 50 |
| 2-8 | CH$_3$CN | Et$_3$N(72) | 100 | 100 | 14 | 100 | 85 |
| 2-9 | HMPA | Et$_3$N(72) | 100 | 100 | 3 | 100 | — |
| 2-10 | HMPA | Et$_3$N(5.5) | 100 | 100 | 2 | 100 | — |
| 2-11 | 1-methyl-2-pyrrolidone | Et$_3$N(72) | 100 | 100 | 7 | 70 | — |

5 mmol of I-1, 20 mmol of II-1 and 0.25 mmol of PdCl$_2$(PPh$_3$)$_2$ were used.
*The conversion and the isolated yield were calculated base on I-1.

TABLE 3

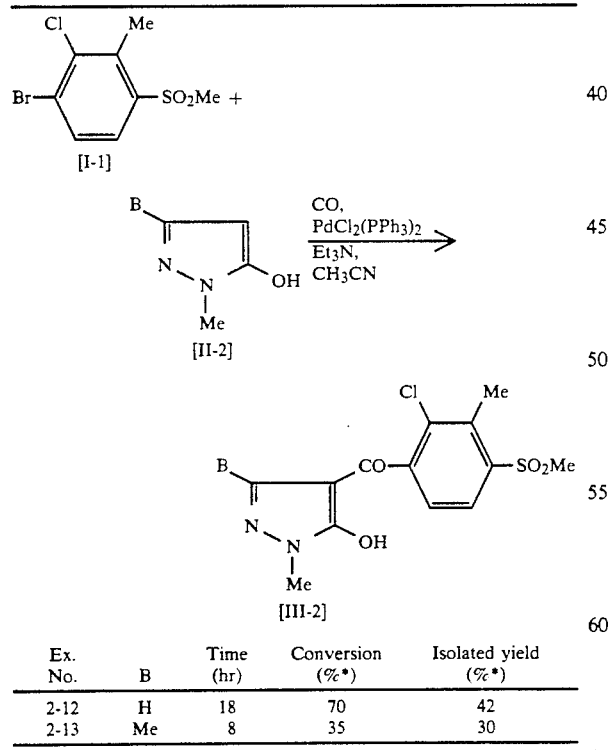

| Ex. No. | B | Time (hr) | Conversion (%*) | Isolated yield (%*) |
|---|---|---|---|---|
| 2-12 | H | 18 | 70 | 42 |
| 2-13 | Me | 8 | 35 | 30 |

I-1: 5 mmol, II-2: 20 mmol, PdCl$_2$(PPh$_3$)$_2$: 0.25 mmol, Et$_3$N: 72 mmol, CH$_3$CN: 50 ml,
CO pressure: 100 kg/cm$^2$, Reaction temp.: 100° C.
*based on I-1.

TABLE 4

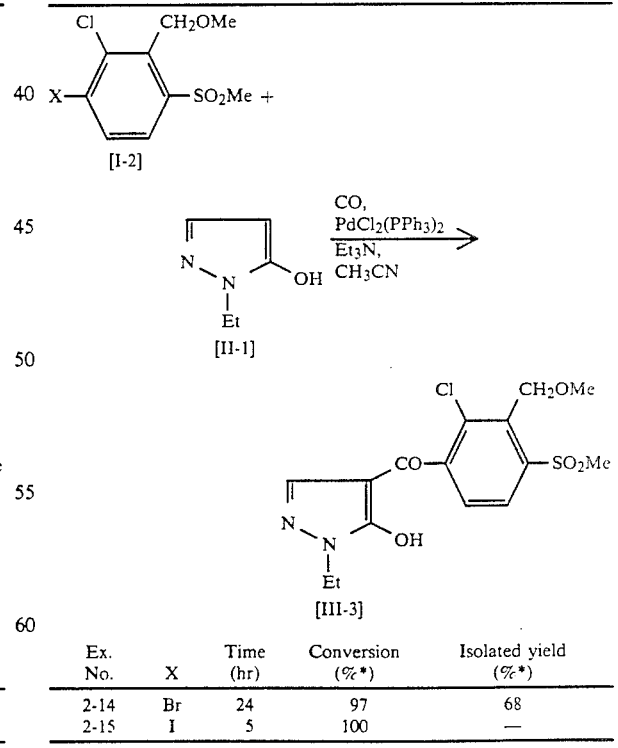

| Ex. No. | X | Time (hr) | Conversion (%*) | Isolated yield (%*) |
|---|---|---|---|---|
| 2-14 | Br | 24 | 97 | 68 |
| 2-15 | I | 5 | 100 | — |

I-1: 5 mmol, II-1: 20 mmol, PdCl$_2$(PPh$_3$)$_2$: 0.25 mmol, Et$_3$N: 72 mmol, CH$_3$CN: 50 ml,
CO pressure: 100 kg/cm$^2$, Reaction temp.: 100° C.
*Based on I-2.

TABLE 5

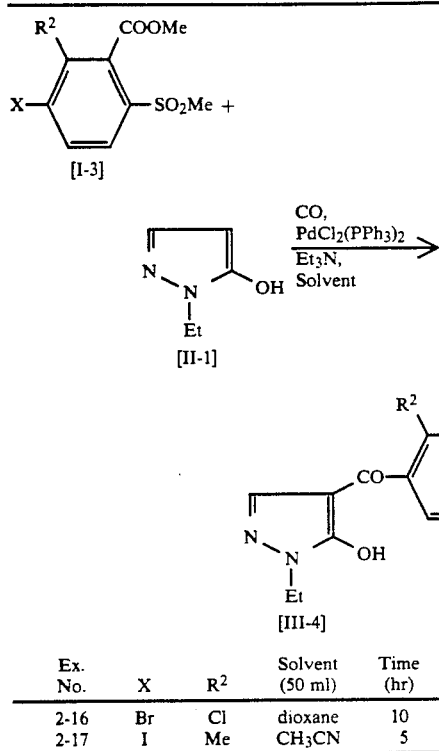

| Ex. No. | X | $R^2$ | Solvent (50 ml) | Time (hr) | Conversion (%*) |
|---|---|---|---|---|---|
| 2-16 | Br | Cl | dioxane | 10 | 80 |
| 2-17 | I | Me | $CH_3CN$ | 5 | 100 |

I-3: 5 mmol, II-1: 20 mmol, $PdCl_2(PPh_3)_2$: 0.25 mmol, $Et_3N$: 72 mmol, $CH_3CN$: 50 ml,
CO Pressure: 100 kg/cm², Reaction temp.: 100° C.
*Based on I-3.

TABLE 6

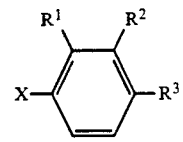

| A | B | $R^1$ | $R^2$ | $R^3$ | m.p. (°C.) |
|---|---|---|---|---|---|
| Me | H | Me | $CH_2OMe$ | $SO_2Me$ | Oily |
| Et | H | Me | $CH_2OMe$ | $SO_2Me$ | 116~118 |
| i-Pr | H | Me | $CH_2OMe$ | $SO_2Me$ | Oily |
| Me | H | Me | $CO_2H$ | $SO_2Me$ | 274~274.5 |
| Me | H | Me | $CO_2Me$ | $SO_2Me$ | 199~201 |
| Et | H | Me | $CO_2Me$ | $SO_2Me$ | 150~152 |
| Me | H | Me | $CO_2Et$ | $SO_2Me$ | 174~174.5 |
| Et | H | Me | $CO_2Et$ | $SO_2Me$ | 78~81 |
| Me | H | Me | $CO_2Pr$-i | $SO_2Me$ | 192~194 |
| Et | H | Me | $CO_2Pr$-i | $SO_2Me$ | 125~128 |
| Me | H | Cl | $CO_2Me$ | Cl | 123~126 |
| Me | H | Me | $CH_2OEt$ | $SO_2Me$ | 178~179 |
| Et | H | Me | $CH_2OEt$ | $SO_2Me$ | Oily |
| i-Pr | H | Me | $CH_2OEt$ | $SO_2Me$ | Oily |
| Me | Me | Me | $CH_2OEt$ | $SO_2Me$ | Oily |
| Me | H | Me | CHMeOMe | $SO_2Me$ | 238~240 |
| Et | H | Me | CHMeOMe | $SO_2Me$ | 138~141 |
| Me | H | Cl | $CH_2OMe$ | $SO_2Me$ | 189~190 |
| Et | H | Cl | $CH_2OMe$ | $SO_2Me$ | 151~154 |
| i-Pr | H | Cl | $CH_2OMe$ | $SO_2Me$ | 142~144 |
| Et | H | Me | $CH_2OPr$-i | $SO_2Me$ | 125~127 |
| Me | H | Me | $CO_2CH_2CH_2OMe$ | $SO_2Me$ | 114~117 |
| Et | H | Me | $CO_2CH_2CH_2OMe$ | $SO_2Me$ | 122~124 |
| Me | H | Cl | $CH_2OCH_2CH_2OMe$ | $SO_2Me$ | 157~161 |
| Et | H | Me | $CO_2Pr$-n | $SO_2Me$ | Oily |
| Me | H | Cl | $CO_2Me$ | $SO_2Me$ | 183~185 |
| Et | H | Cl | $CO_2Me$ | $SO_2Me$ | 174~176 |

TABLE 6-continued

| A | B | $R^1$ | $R^2$ | $R^3$ | m.p. (°C.) |
|---|---|---|---|---|---|
| i-Pr | H | Cl | $CO_2Me$ | $SO_2Me$ | 138~140 |
| Me | H | OMe | $CO_2Me$ | $SO_2Me$ | 195~198 |
| Me | H | Cl | $CO_2Pr$-i | $SO_2Me$ | 117~119 |
| Et | H | Cl | $CO_2Pr$-i | $SO_2Me$ | 141~143 |
| i-Pr | H | Me | $CO_2Me$ | $SO_2Me$ | 116~121 |
| Me | H | OMe | $CH_2OMe$ | $SO_2Me$ | 154~157 |
| Et | H | OMe | $CO_2Me$ | $SO_2Me$ | 172~175 |
| Et | H | Cl | $CO_2Me$ | Cl | 167~170 |
| i-Pr | H | Cl | $CO_2Me$ | Cl | 144~151 |
| Et | H | Me | $CO_2Me$ | SMe | 142~146 |
| Et | H | Cl | $CH_2OMe$ | Cl | 102~104 |
| Et | H | Cl | $CO_2Et$ | $SO_2Me$ | 100~104 |
| Et | H | Me | $CH_2OMe$ | SMe | Oily |
| Me | H | Cl | $CH_2OMe$ | Cl | 141~144 |
| i-Pr | H | Cl | $CO_2Et$ | $SO_2Me$ | 123~126 |
| Et | H | OMe | $CH_2OMe$ | $SO_2Me$ | Oily |
| Et | H | Me | CHMeOEt | $SO_2Me$ | Oily |
| Et | H | Me | CHEtOMe | $SO_2Me$ | Oily |
| Me | H | Cl | OMe | $SO_2Me$ | 229~231 |
| Et | H | Cl | OMe | $SO_2Me$ | 196~198 |
| Me | H | OMe | H | $SO_2Me$ | 202~206 |
| Et | H | Cl | OPr | $SO_2Me$ | 149~151 |
| Et | H | Cl | OPr-i | $SO_2Me$ | 142~145 |
| Et | H | Cl | OEt | $SO_2Me$ | 170~174 |
| Me | H | Cl | OMe | $SO_2Me$ | 229~231 |
| Et | H | Cl | OMe | $SO_2Me$ | 196~198 |
| Et | H | Me | OMe | $SO_2Me$ | 157~159 |
| i-Pr | H | Me | OMe | $SO_2Me$ | 135~137 |

What is claimed is:

1. A substituted benzene of the formula I':

selected from the group consisting of wherein:
a) X is I, $R^1$ is CN, $R^2$ is H and $R^3$ is SMe,
b) X is I, $R^1$ is OMe, $R^2$ is H and $R^3$ is SMe,
c) X is Br, $R^1$ is Cl, $R^2$ is $CO_2Me$ and $R^3$ is $SO_2Me$,
d) X is Br, $R^1$ is Cl, $R^2$ is $CO_2H$ and $R^3$ is $SO_2Me$,
e) X is I, $R^1$ is Cl, $R^2$ is $CO_2Me$ and $R^3$ is SMe,
f) X is I, $R^1$ is Cl, $R^2$ is $Co_2H$ and $R^3$ is SMe,
g) X is I, $R^1$ is Cl, $R^2$ is $CO_2Pr$-i and $R^3$ is SMe,
h) X is Br, $R^1$ is Me, $R^2$ is $CO_2Me$ and $R^3$ is SMe,
i) X is Br, $R^1$ is Me, $R^2$ $CO_2H$ and $R^3$ is SMe,
j) X is I, $R^1$ is Me, $R^2$ is $CO_2Pr$-i and $R^3$ is SMe,
k) X is I, $R^1$ is Me, $R^2$ is $CO_2Me$ and $R^3$ is SMe,
l) X is I, $R^1$ is Me, $R^2$ is $CO_2Me$ and $R^3$ is $SO_2Me$,
m) X is I, $R^1$ is Me, $R^2$ is $CO_2Et$ and $R^3$ is SMe,
n) X is I, $R^1$ is Me, $R^2$ is $CO_2Pr$-i and $R^3$ is SMe,
o) X is I, $R^1$ is Me, $R^2$ is $CO_2CH_2CH_2OMe$ and $R^3$ is SMe,
p) X is I, $R^1$ is Me, $R^2$ is $CO_2CH_2CH_2Cl$ and $R^3$ is SMe,
q) X is I, $R^1$ is OMe, $R^2$ is $CO_2Me$ and $R^3$ is SMe,
r) X is Br, $R^1$ is Cl, $R^2$ is $CH_2OMe$ and $R^3$ is $SO_2Me$, s) X is I, $R^1$ is Cl, $R^2$ is $CH_2OMe$ and $R^3$ is SMe,
t) X is I, $R^1$ is Me, $R^2$ is $CH_2OMe$ and $R^3$ is $SO_2Me$,
u) X is I, $R^1$ is Me, $R^2$ is $CH_2OMe$ and $R^3$ is SMe,
v) X is I, $R^1$ is Me, $R^2$ is $CH_2OEt$ and $R^3$ is SMe,
w) X is I, $R^1$ is Me, $R^2$ is $CH_2OPr$-i and $R^3$ is SMe,
x) X is I, $R^1$ is OMe, $R^2$ is $CH_2OMe$ and $R^3$ is SMe,
y) X is I, $R^1$ is Me, $R^2$ is CHMeOMe and $R^3$ is SMe,
z) X is I, $R^1$ is Me, $R^2$ is CHMeOEt and $R^3$ is SMe,
aa) X is I, $R^1$ is Me, $R^2$ is CHEtOMe and $R^3$ is SMe,
bb) X is I, $R^1$ is Me, $R^2$ is OMe and $R^3$ is SMe,
cc) X is I, $R^1$ is Cl, $R^2$ is Cl and $R^3$ is SMe,
dd) X is I, $R^1$ is Me, $R^2$ is $NO_2$ and $R^3$ is SMe,
ee) X is Br, $R^1$ is Cl, $R^2$ is Me and $R^3$ is $SO_2Me$,
ff) X is Br, $R^1$ is Cl, $R^2$ is Me and $R^3$ is SMe,
gg) X is Br, $R^1$ is Cl, $R^2$ is $CH_2OPr$-i and $R^3$ is $SO_2Me$.

2. A substituted benzene as defined in claim 1, wherein X is I, $R^1$ is CN, $R^2$ is H and $R^3$ is SMe.

3. A substituted benzene as defined in claim 1, wherein X is I, $R^1$ is OMe, $R^2$ is H and $R^3$ is SMe.

4. A substituted benzene as defined in claim 1, wherein X is Br, $R^1$ is Cl, $R^2$ is $CO_2Me$ and $R^3$ is $SO_2Me$.

5. A substituted benzene as defined in claim 1, wherein X is Br, $R^1$ is Cl, $R^2$ is $CO_2H$ and $R^3$ is $SO_2Me$.

6. A substituted benzene as defined in claim 1, wherein X is I, $R^1$ is Cl, $R^2$ is $CO_2Me$ and $R^3$ is SMe.

7. A substituted benzene as defined in claim 1, wherein X is I, $R^1$ is Cl, $R^2$ is $CO_2H$ and $R^3$ is SMe.

8. A substituted benzene as defined in claim 1, wherein X is I, $R^1$ is Cl, $R^2$ is $CO_2Pr$-i and $R^3$ is SMe.

9. A substituted benzene as defined in claim 1, wherein X is Br, $R^1$ is Me, $R^2$ is $CO_2Me$ and $R^3$ is SMe.

10. A substituted benzene as defined in claim 1, wherein X is Br, $R^1$ is Me, $R^2$ is $CO_2H$ and $R^3$ is SMe.

11. A substituted benzene as defined in claim 1, wherein X is Br, $R^1$ is Me, $R^2$ is $CO_2H$ and $R^3$ is SMe.

12. A substituted benzene as defined in claim 1, wherein X is I, $R^1$ is Me, $R^2$ is $CO_2Me$ and $R^3$ is SMe.

13. A substituted benzene as defined in claim 1, wherein X is I, $R^1$ is Me, $R^2$ is $CO_2Me$ and $R^3$ is $SO_2Me$.

14. A substituted benzene as defined in claim 1, wherein X is I, $R^1$ is Me, $R^2$ is $CO_2Et$ and $R^3$ is SMe.

15. A substituted benzene as defined in claim 1, wherein X is I, $R^1$ is Me, $R^2$ is $CO_2Pr$-i and $R^3$ is SMe.

16. A substituted benzene as defined in claim 1, wherein X is I, $R^1$ is Me, $R^2$ is $CO_2CH_2CH_2OMe$ and $R^3$ is SMe.

17. A substituted benzene as defined in claim 1, wherein X is I, $R^1$ is Me, $R^2$ is $CO_2CH_2CH_2Cl$ and $R^3$ is SMe.

18. A substituted benzene as defined in claim 1, wherein X is I, $R^1$ is OMe, $R^2$ is $CO_2Me$ and $R^3$ is SMe.

19. A substituted benzene as defined in claim 1, wherein X is Br, $R^1$ is Cl, $R^2$ is $CH_2OMe$ and $R^3$ is $SO_2Me$.

20. A substituted benzene as defined in claim 1, wherein X is I, $R^1$ is Cl, $R^2$ is $CH_2OMe$ and $R^3$ is SMe.

21. A substituted benzene as defined in claim 1, wherein X is I, $R^1$ is Me, $R^2$ is $CH_2OMe$ and $R^3$ is $SO_2Me$.

22. A substituted benzene as defined in claim 1, wherein X is I, $R^1$ is Me, $R^2$ is $CH_2OMe$ and $R^3$ is SMe.

23. A substituted benzene as defined in claim 1, wherein X is I, $R^1$ is Me, $R^2$ is $CH_2OEt$ and $R^3$ is SMe.

24. A substituted benzene as defined in claim 1, wherein X is I, $R^1$ is Me, $R^2$ is $CH_2OPr$-i and $R^3$ is SMe.

25. A substituted benzene as defined in claim 1, wherein X is I, $R^1$ is OMe, $R^2$ is $CH_2OMe$ and $R^3$ is SMe.

26. A substituted benzene as defined in claim 1, wherein X is I, $R^1$ is Me, $R^2$ is CHMeOMe and $R^3$ is SMe.

27. A substituted benzene as defined in claim 1, wherein X is I, $R^1$ is Me, $R^2$ is CHMeOEt and $R^3$ is SMe.

28. A substituted benzene as defined in claim 1, wherein X is I, $R^1$ is Me, $R^2$ is CHEtOMe and $R^3$ is SMe.

29. A substituted benzene as defined in claim 1, wherein X is I, $R^1$ is Me, $R^2$ is OMe and $R^3$ is SMe.

30. A substituted benzene as defined in claim 1, wherein X is I, $R^1$ is Cl, $R^2$ is Cl and $R^3$ is SMe.

31. A substituted benzene as defined in claim 1, wherein X is I, $R^1$ is Me, $R^2$ is $NO_2$ and $R^3$ is SMe.

32. A substituted benzene as defined in claim 1, wherein X is Br, $R^1$ is Cl, $R^2$ is Me and $R^3$ is $SO_2Me$.

33. A substituted benzene as defined in claim 1, wherein X is Br, $R^1$ is Cl, $R^2$ is Me and $R^3$ is SMe.

34. A substituted benzene as defined in claim 1, wherein X is Br, $R^1$ is Cl, $R^2$ is $CH_2OPr$-i and $R^3$ is $SO_2Me$.

* * * * *